United States Patent
Wogoman et al.

(10) Patent No.: US 12,036,128 B2
(45) Date of Patent: Jul. 16, 2024

(54) ADJUSTABLE TIBIAL TRIAL INSTRUMENT AND ORTHOPAEDIC SURGICAL METHOD OF USING THE SAME

(71) Applicant: DEPUY IRELAND UNLIMITED COMPANY, Ringaskiddy (IE)

(72) Inventors: Thomas E. Wogoman, Warsaw, IN (US); James E. Barnett, Leeds (GB); Michael J. Rock, Leeds (GB); Alasdair Mercer, Warsaw, IN (US); Daniel M. Hippensteel, Fort Wayne, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 0 days.

(21) Appl. No.: 18/127,078

(22) Filed: Mar. 28, 2023

(65) Prior Publication Data

US 2023/0225874 A1 Jul. 20, 2023

Related U.S. Application Data

(62) Division of application No. 17/015,460, filed on Sep. 9, 2020, now Pat. No. 11,612,488.

(60) Provisional application No. 62/898,237, filed on Sep. 10, 2019.

(51) Int. Cl.
*A61F 2/38* (2006.01)
*A61F 2/30* (2006.01)
*A61F 2/46* (2006.01)

(52) U.S. Cl.
CPC .......... *A61F 2/389* (2013.01); *A61F 2/30771* (2013.01); *A61F 2/461* (2013.01); *A61F 2/4684* (2013.01); *A61F 2002/30537* (2013.01); *A61F 2002/30841* (2013.01)

(58) Field of Classification Search
CPC .................... A61F 2/389; A61F 2/4684; A61F 2002/30537; A61F 2/3886; A61F 2002/4625; A61F 2002/4627; A61F 2/461
See application file for complete search history.

(56) References Cited

U.S. PATENT DOCUMENTS

| 5,733,292 | A | 3/1998 | Gustilo et al. |
| 2003/0109929 | A1 | 6/2003 | Keller |
| 2006/0111790 | A1 | 5/2006 | Dietz |
| 2010/0250571 | A1* | 9/2010 | Pierce ................. A61B 5/4528 600/587 |
| 2012/0158152 | A1 | 6/2012 | Claypool et al. |

(Continued)

FOREIGN PATENT DOCUMENTS

| EP | 1025818 A2 | 8/2000 |
| EP | 1974694 A1 | 10/2008 |

(Continued)

OTHER PUBLICATIONS

PCT International Search Report, International Application No. PCT/EP2020/075187; date of mailing Nov. 23, 2020; 13 pages.

*Primary Examiner* — Javier G Blanco
(74) *Attorney, Agent, or Firm* — Barnes & Thornburg LLP

(57) ABSTRACT

An orthopaedic surgical system for use in implanting a total knee prosthesis includes an adjustable tibial trial component that is movable in the anterior/posterior direction and rotatable when installed on the resected surface of a patient's tibia. A method of using such a system is also disclosed.

4 Claims, 14 Drawing Sheets

(56) References Cited

U.S. PATENT DOCUMENTS

| | | | |
|---|---|---|---|
| 2013/0102929 A1* | 4/2013 | Haight | A61B 17/025 600/587 |
| 2017/0156736 A1 | 6/2017 | Claypool et al. | |
| 2017/0333058 A1* | 11/2017 | Cabot | A61F 2/389 |
| 2021/0068962 A1 | 3/2021 | Wogoman et al. | |

FOREIGN PATENT DOCUMENTS

| | | |
|---|---|---|
| EP | 2644107 A1 | 10/2013 |
| WO | 2017181216 A1 | 10/2017 |

* cited by examiner

ADJUSTABLE TIBIAL TRIAL INSTRUMENT AND ORTHOPAEDIC SURGICAL METHOD OF USING THE SAME

This application is a divisional of U.S. patent application Ser. No. 17/015,460 filed on Sep. 9, 2020, now U.S. Pat. No. 11,612,488, which claims priority under 35 U.S.C. § 119 to U.S. Provisional Patent Application Ser. No. 62/898,237 which was filed on Sep. 10, 2019, the entireties of each of which is incorporated herein by reference.

TECHNICAL FIELD

The present disclosure relates to orthopaedic surgical instruments, and, more specifically, to orthopaedic surgical instruments for implanting an orthopaedic knee prosthesis during a total knee arthroplasty procedure.

BACKGROUND

Total knee replacement (TKR), also referred to as total knee arthroplasty (TKA), is a surgical procedure where worn, diseased, or damaged surfaces of a knee joint are removed and replaced with artificial surfaces. An orthopaedic knee prosthesis generally has three components: a distal femoral component, a proximal tibial component, and a bearing component positioned therebetween.

SUMMARY

According to one aspect of the disclosure, an orthopaedic surgical system for use in implanting a total knee prosthesis includes an adjustable tibial trial instrument that includes a tibial plate. An attachment mechanism is configured to secure the tibial plate to a resected planar surface of the tibia of a patient. The tibial trial instrument also includes an adjustment mechanism that operable to both rotate and move the tibial plate in the anterior/posterior direction relative to resected planar surface when the tibial trial instrument is secured to the tibia of the patient. The surgical system also includes a tibial insert trial that is secured to the tibial trial instrument.

According to another aspect, a method of performing an orthopaedic surgical procedure includes securing a tibial trial instrument to a proximal end of a patient's tibia, and thereafter securing tibial insert trial to the tibial trial instrument. The method also includes operating an adjustment mechanism of the tibial trial instrument so as to move the tibial insert trial in the anterior/posterior direction. Operation of the adjustment mechanism of the tibial trial instrument rotates the tibial insert trial.

According to yet another aspect, an orthopaedic surgical system for use in implanting a total knee prosthesis includes an adjustable tibial trial instrument. The adjustable tibial trial instrument has a tibial plate and an attachment mechanism configured to secure the tibial plate to a surgically-prepared planar surface of the tibia of a patient. The adjustable tibial trial instrument also includes an adjustment mechanism that is operable to move the tibial plate in the anterior/posterior direction relative to the resected planar surface and also rotate the tibial plate relative to the resected planar surface when the tibial trial instrument is secured to the tibia of the patient. The orthopaedic surgical system also includes a tibial insert trial secured to the tibial trial instrument.

In an embodiment, the adjustment mechanism includes a first knob operatively coupled to a first shuttle and a second knob operatively coupled to a second shuttle. In such an embodiment, rotation of the first knob causes the first shuttle to move relative to the tibial plate, with rotation of the second knob causing the second shuttle to move relative to the tibial plate. The attachment mechanism of the adjustable tibial trial instrument may also include a first bone-engaging spike secured to the first shuttle and a second bone-engaging spike secured to the second shuttle.

In an embodiment, rotation of both the first knob and the second knob in the same direction and through the same rotational distance causes the tibial plate to move linearly relative to the bone-engaging spikes when the tibial trial instrument is secured to the tibia of the patient.

In such an embodiment, rotation of both the first knob and the second knob in opposite directions causes the tibial plate to rotate relative to the bone-engaging spikes when the tibial trial instrument is secured to the tibia of the patient. Moreover, rotation of both the first knob and the second knob through a different rotational distance may cause the tibial plate to rotate relative to the bone-engaging spikes when the tibial trial instrument is secured to the tibia of the patient.

The orthopaedic surgical system may also include a sizing template that is the same size and shape as the tibial plate. The sizing template may include a first closed slot and a second closed slot formed therein, both of which have posterior ends that open into a posterior edge of the sizing template. In such an embodiment, both of the first closed slot and the second closed slot are sized to receive, and closely conform to, a pair of bone-engaging spikes of the adjustable tibial trial instrument.

The orthopaedic surgical system may also include a position transfer instrument and a non-adjustable tibial trial instrument. In such an arrangement, both the adjustable tibial trial instrument and the non-adjustable trial instrument have plate openings defined therein, with such plate openings having a similar size and shape as an outer periphery of the position transfer instrument such that the position transfer instrument closely conforms to the plate openings when positioned therein.

According to another aspect, an orthopaedic surgical system for use in implanting a total knee prosthesis includes an adjustable tibial trial instrument. The adjustable tibial trial instrument includes a tibial plate having a pair of channels formed therein, along with a pair of shuttles. One of the shuttles is positioned in each of the pair of channels. Each of the shuttles has a bone-engaging spike extending from its inferior surface, with such bone-engaging spikes being configured to secure the tibial plate to a surgically-prepared planar surface of the tibia of a patient. The adjustable tibial trial instrument also includes a pair of thumbscrews, each of which is threadingly engaged with one of the shuttles such that rotation thereof causes the shuttle to translate within the channel in which it is positioned. Rotation of one or both of the pair of thumbscrews is operable to move the tibial plate in the anterior/posterior direction relative to the resected planar surface and rotate the tibial plate relative to the resected planar surface when the tibial trial instrument is secured to the tibia of the patient. The orthopaedic surgical system also includes a tibial insert trial secured to the tibial trial instrument.

In an embodiment, each of the pair of thumbscrews includes a knob such that rotation of the knob causes rotation of the thumbscrew.

Rotation of the pair of thumbscrews in the same direction and through the same rotational distance may cause the tibial plate to move linearly relative to the resected planar surface when the tibial trial instrument is secured to the tibia of the patient.

Rotation of the pair of thumbscrews in opposite directions of one another may cause the tibial plate to rotate relative to the resected planar surface when the tibial trial instrument is secured to the tibia of the patient.

Rotation of the pair of thumbscrews through a different rotational distance relative to the other may cause the tibial plate to rotate relative to the resected planar surface when the tibial trial instrument is secured to the tibia of the patient.

The orthopaedic surgical system may further include a sizing template which is the same size and shape as the tibial plate. In such an arrangement, the sizing template has a pair of closed slots formed therein, with both of such closed slots having posterior ends that open into a posterior edge of the sizing template. The closed slots are sized to receive, and closely conform to, the bone-engaging spikes of the adjustable tibial trial instrument.

In an embodiment of this aspect, the orthopaedic surgical system may also include a position transfer instrument and a non-adjustable tibial trial instrument. In such an arrangement, both the adjustable tibial trial instrument and the non-adjustable trial instrument have plate openings defined therein, with such plate openings having a similar size and shape as an outer periphery of the position transfer instrument such that the position transfer instrument closely conforms to the plate openings when positioned therein.

According to another aspect, a method of performing an orthopaedic surgical procedure includes securing an adjustable tibial trial instrument to a surgically-prepared proximal end of a patient's tibia. A tibial insert trial is secured to the adjustable tibial trial instrument. A femoral trial component is secured to a surgically-prepared distal end of the patient's femur. The femoral trial component is positioned into contact with the tibial insert trial, and the patient's tibia is moved relative to the patient's femur through a trial range of motion. An adjustment mechanism of the adjustable tibial trial instrument is operated so as to move the tibial insert trial relative to the surgically-prepared proximal end of the patient's tibia.

The adjustment mechanism of the adjustable tibial trial instrument may be operated so as to move the tibial insert trial relative to the surgically-prepared proximal end of the patient's tibia in the anterior/posterior direction.

The adjustment mechanism of the adjustable tibial trial instrument may be operated so as to rotate the tibial insert trial relative to the surgically-prepared proximal end of the patient's tibia.

The adjustment mechanism of the adjustable tibial trial instrument may be operated by rotating one or both of a pair of knobs of the adjustable tibial trial instrument so as to move the tibial insert trial relative to the surgically-prepared proximal end of the patient's tibia.

The adjustable tibial trial instrument may be secured to the surgically-prepared proximal end of the patient's tibia first positioning a sizing template on the surgically-prepared proximal end of the patient's tibia and thereafter advancing a pair of bone-engaging spikes of the adjustable tibial trial instrument into a pair of slots formed in the sizing template. The adjustable tibial trial instrument may then be impacted so as to drive the bone-engaging spikes into the surgically-prepared proximal end of the patient's tibia to an initial depth. The sizing template may then be removed from the surgically-prepared proximal end of the patient's tibia. The adjustable tibial trial instrument is then impacted so as to drive the bone-engaging spikes into the surgically-prepared proximal end of the patient's tibia to a final depth.

The method may also include positioning a position transfer instrument in a plate opening defined in the adjustable tibial trial instrument and thereafter impacting the position transfer instrument so as to secure it to the surgically-prepared proximal end of the patient's tibia. The adjustable tibial trial instrument may then be removed from the surgically-prepared proximal end of the patient's tibia. A non-adjustable tibial trial instrument may then be positioned on the surgically-prepared proximal end of the patient's tibia such that the position transfer instrument is received into a plate opening defined in the non-adjustable tibial trial instrument and thereafter securing the non-adjustable tibial trial instrument to the surgically-prepared proximal end of the patient's tibia.

BRIEF DESCRIPTION OF THE DRAWINGS

The detailed description particularly refers to the following figures, in which.

DETAILED DESCRIPTION OF THE DRAWINGS

Figure 1:
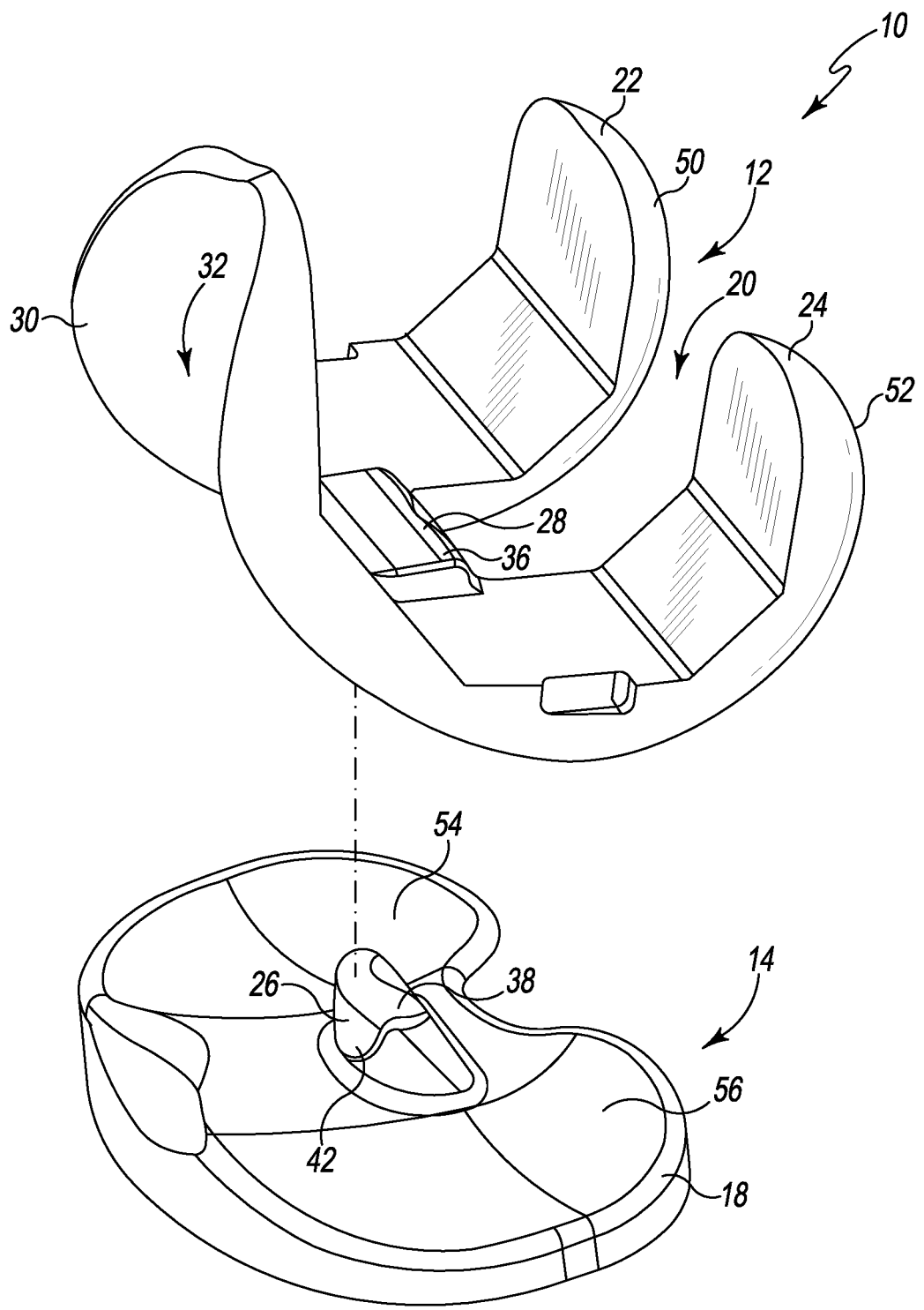
FIG. 1 is an exploded perspective view of an ACL substituting knee prosthesis.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring now to FIG. 1, there is shown an exemplary embodiment of an orthopedic knee prosthesis 10 for use in total knee arthroplasty procedures. The prosthesis 10 includes a femoral component 12 and a tibial component 14 that is configured to permit the femoral component 12 to articulate over a range of flexion. In this exemplary embodiment, the tibial component 14 includes a tibial tray insert 18, which is configured to be attached to, for example, a tibial tray (not shown) secured to the proximal end of a patient's tibia. Such trays may include stems configured to be received within the intramedullary canal of the tibia. It should be appreciated that the tray may provide either a fixed bearing interface to lock the orientation of the tibial tray insert 18 with the tibial tray or a mobile bearing interface that allows the tibial tray insert 18 to move independent of the tibial tray. Additionally, in other embodiments, the tibial tray and the tibial tray insert may be combined into a single, monolithic component.

The femoral component 12 is illustratively formed from a metallic material such as cobalt-chromium or titanium, but may be formed from other materials, such as a ceramic material, a polymer material, a bio-engineered material, or the like. The tibial tray insert 18 is illustratively formed from a polymer material such as an ultra-high molecular weight polyethylene (UHMWPE), but may be formed from other materials, such a ceramic material, a metallic material, a bio-engineered material, or the like.

As shown in FIG. 1, the femoral component 12 is illustratively a posterior cruciate retaining orthopedic femoral component that includes a posterior discontinuity or gap 20 between lateral and medial condyles 22, 24 to allow the femoral component to articulate between maximum extension and maximum flexion without impinging the posterior cruciate ligament (PCL), which is retained during the total arthroplasty procedure. In contrast, the anterior cruciate ligament (ACL) is sacrificed or removed during a total arthroplasty procedure. Those skilled in the art are familiar with the posterior constraint resulting from retention of the posterior cruciate ligament, whereas those skilled in the art are also familiar with the absence of anterior constraint resulting from the absence of the anterior cruciate ligament.

The exemplary femoral component 12 includes a pair of condyles 22, 24, each of which has an arcuate shape in order to allow for smooth articulation of the femur with respect to the tibia. The anterior portion 26 of the femoral component 12 includes a front exterior face 30 having a groove 32 configured to receive at least a portion of a patella component (not shown). The femoral component 12 also includes an anterior cam 36 that is configured to engage a post 38 of the tibial component 14.

The knee prosthesis 10 also includes a tibial tray insert 18. As described above, the tibial tray insert 18 includes bearing surfaces 54, 56 that are adapted to receive and engage the condyles 22, 24 of the femoral component 12, respectively. The two bearing surfaces 54, 56 are partially separated from one another by the post 38 which extends superiorly from the tibial tray insert 18. In this exemplary embodiment, the post 38 is integrally formed with the tibial tray insert 18. However, it should be appreciated that the post 38 may be separable from the tibial tray insert 18 and its location is independent of the location/movement of the tibial tray insert.

The post 38 has an anterior surface or wall 26 that is configured to engage the posterior surface 28 of the cam 36 of the femoral component 12 when the implant 10 (and hence the knee) is at full extension and over part of flexion. The post 38 also includes a curved anterior section 42 that is sized to ensure the cam 36 disengages from the post 38. It should be appreciated that the post 38 may include other structures that are sized and shaped to ensure the cam 36 disengages from the post 38.

Referring to FIGS. 2-5, an orthopaedic surgical instrument system 70 is shown. The instrument system 70 is used during an orthopaedic surgical procedure to implant the knee prosthesis 10. Specifically, the instrument system 70 is used by a surgeon during the tibial trialing procedure to size and select the tibial components (i.e., the tibial tray and tibial insert) of the knee prosthesis 10.

Figure 2:
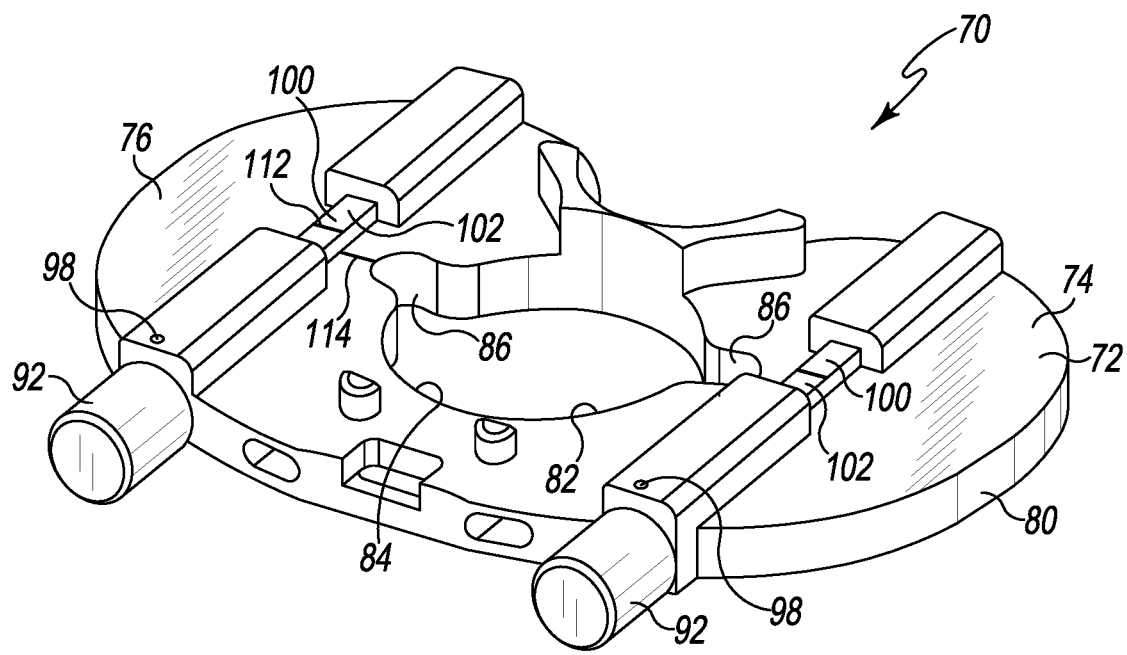
FIG. 2 is a perspective view showing the superior side of an adjustable tibial trial instrument used in an orthopaedic surgical procedure to implant the knee prosthesis of FIG. 1.

As can be seen in FIG. 2, the instrument system 70 includes an adjustable tibial trial instrument 72. As will be discussed in greater detail below, the tibial trial instrument 72 may be used to during the trialing process to adjust the position of the tibial trial insert in the anterior/posterior direction and rotational direction without removing the trial components or distracting the ligaments of the patient's knee.

The tibial trial instrument 72 includes a plate 74 having an upper surface 76, a lower surface 78, and an outer sidewall 80 extending between the surfaces 76, 78. The plate 74 has a plate opening 82 defined in the upper surface 74. The plate opening 82 has a central opening 84 and a pair of elongated openings 86 extending outwardly therefrom. As will be discussed in greater detail below, the configuration of the plate opening 82 permits the installation of a transfer button into the proximal end of the patient's tibia. In some embodiments, the configuration of the plate opening 82 also permits the advancement of various surgical drills, punches, and other instruments into the proximal end of the patient's tibia. It should be appreciated that the tibial trial instrument 72 may be provided in a number of different sizes to accommodate tibias of various sizes.

Figure 3:
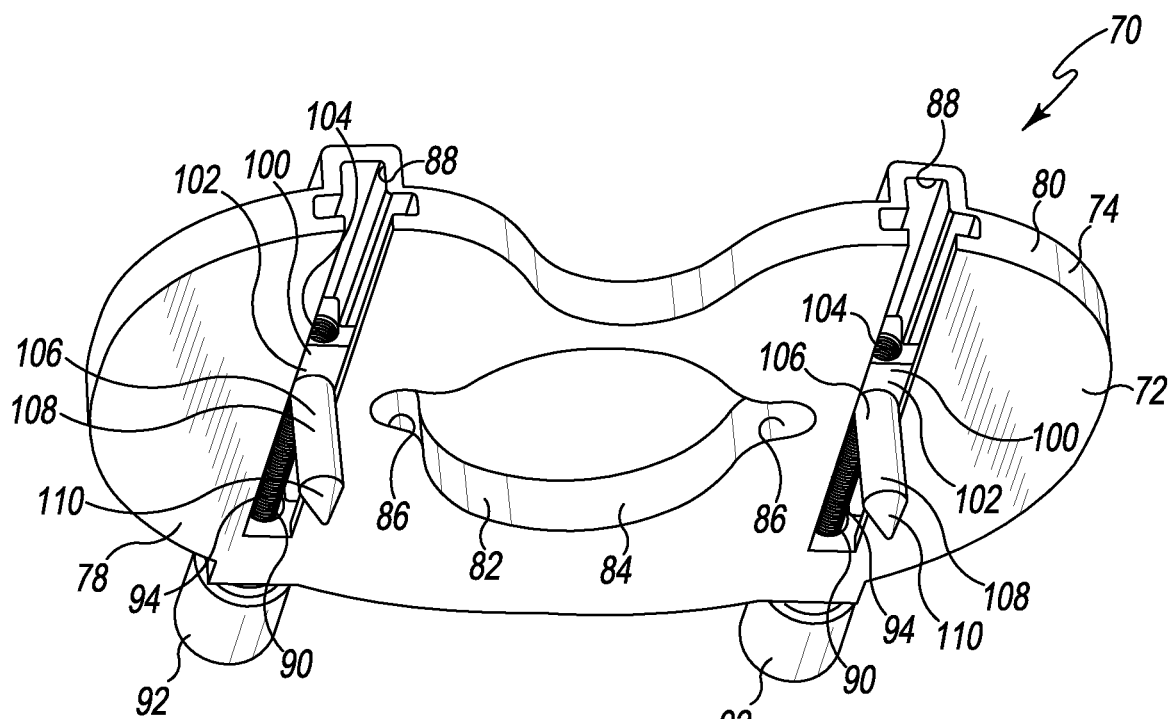
FIG. 3 is a view similar to FIG. 2, but showing the inferior side of the adjustable tibial trial instrument.
Figure 4:
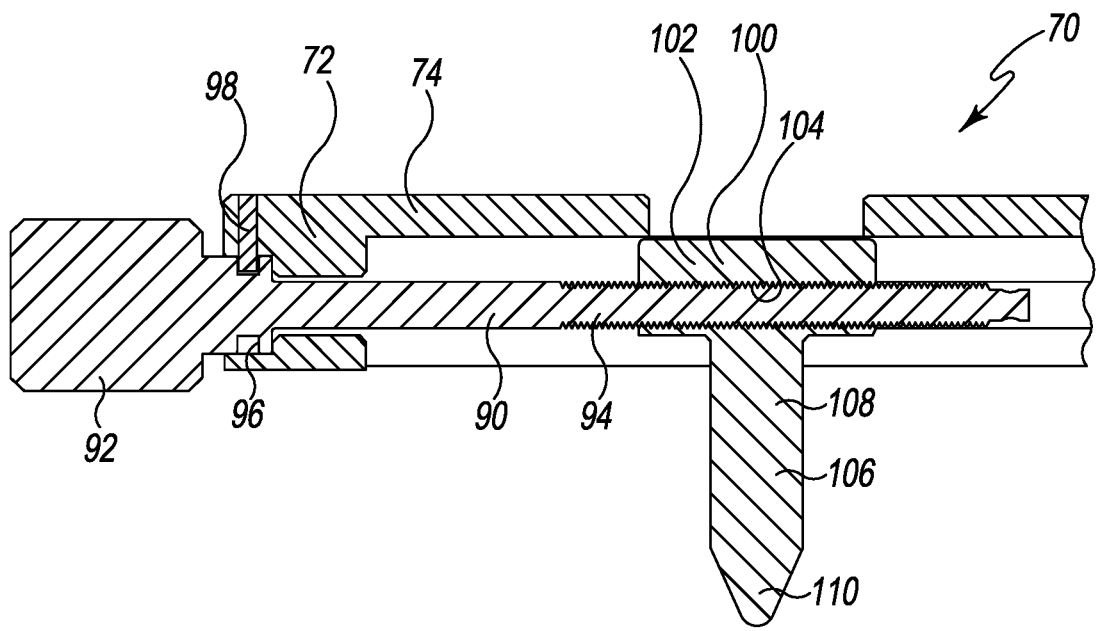
FIG. 4 is cross-sectional view taken along the line 4-4 of FIG. 2.
Figure 5:
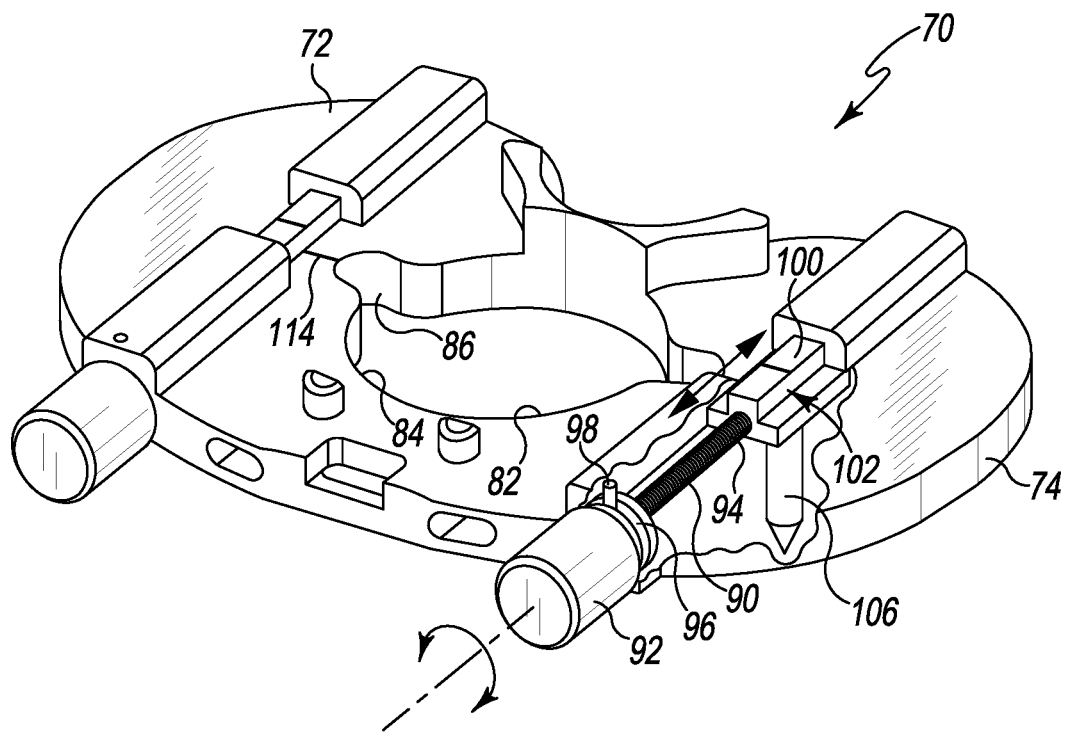
FIG. 5 is a perspective view of the adjustable tibial trial instrument with a portion of its plate cut away.

The plate 74 has a pair of elongated channels 88 formed therein. The channels 88 extend in the anterior/posterior direction. As can be seen in FIG. 3, the channels have a generally T-shaped cross sectional shape. The channels 88 are closed on their anterior end and are open through the outer sidewall 80 on their posterior end. Each of the channels 88 has a thumbscrew 90 captured therein. Specifically, a thumbscrew 90 having a knob 92 and threaded shaft 94 is positioned in each of the channels 88. As can be seen in FIG. 4, the threaded shaft 94 of each of the thumbscrews 90 has an undercut 96 formed therein. A retention pin 98 is secured to the upper surface 76 of the plate near the anterior end of each of the channels 88. The retention pins 98 extend posteriorly into the channels 88 and are captured within the undercuts 96 formed in the threaded shafts 94 of the thumbscrews 90. As such, the retention pins 98 prevent the thumbscrews from backing out of the plate 74 of the tibial trial instrument 72.

As can be seen in FIGS. 2-5, a shuttle 100 is threadingly engaged on each of the threaded shafts 94 of the thumbscrews 90. The upper body 102 of the shuttles 100 is generally T-shaped in cross section and sized to closely conform to the inner surfaces of the channels 88. The upper body 102 of each shuttle 100 has an elongated threaded bore 104 formed therein. The threaded bore 104 extends in the anterior/posterior direction and is sized to threadingly engage the threaded shaft 94 of the thumbscrews 90. In such a way, the shuttles 100 can translate within the channels 88 as a result of rotation of the thumbscrews 90. As such, the thumbscrews 90 and the shuttles 100 define a pair of screw drive mechanisms that, as described further below, allow for rotational movement of the tibial trial instrument 72, along with movement of the tibial trial instrument 72 in the anterior/posterior direction.

As can be seen in FIG. 3, a mounting spike 106 extends downwardly from the inferior surface of each of the shuttles 100. Each spike 106 includes an upper cylindrical section 108 and a pointed conical tip 110 configured to engage the surgically resected proximal end of the patient's tibia thereby temporarily securing the tibial trial instrument 72 to the proximal end of the patient's tibia during a trialing procedure.

As described above, rotation of the thumbscrews 90 causes the shuttles 100 (and hence the spikes 106) to move anteriorly and posteriorly as the upper body 102 of the shuttles 100 translate back and forth within the channels 88 of the tibial trial instrument 72. During such rotation of the thumbscrews 90, the retention pins 98 prevent the thumbscrews 90 from backing out of the plate 74 of the tibial trial instrument 72. As such, if the spikes 106 are held in a fixed position (as is the case when they are driven into the bone tissue of the patient's tibia), rotation of the thumbscrews 90 causes the plate 74 of the tibial trial instrument 72 to move relative to the stationary spikes 106. If both thumbscrews 90 are rotated in the same direction and through the same rotational distance, the plate 74 of the tibial trial instrument 72 moves linearly relative to the stationary spikes 106 (and hence the patient's tibia) in either the anterior or posterior direction (based on which direction the knobs 92 are rotated). If the thumbscrews 90 are rotated in different directions and/or through different rotational distances, the plate 74 of the tibial trial instrument 72 rotates relative to the stationary spikes 106 (and hence the patient's tibia) based on which direction the knobs 92 are rotated. It should be appreciated that the thumbscrews 90 are infinitely-adjustable thereby providing the surgeon with a wide range of options for setting the A/P position and rotational orientation of the tibial trial instrument 72 relative to the patient's tibia.

Figure 11:
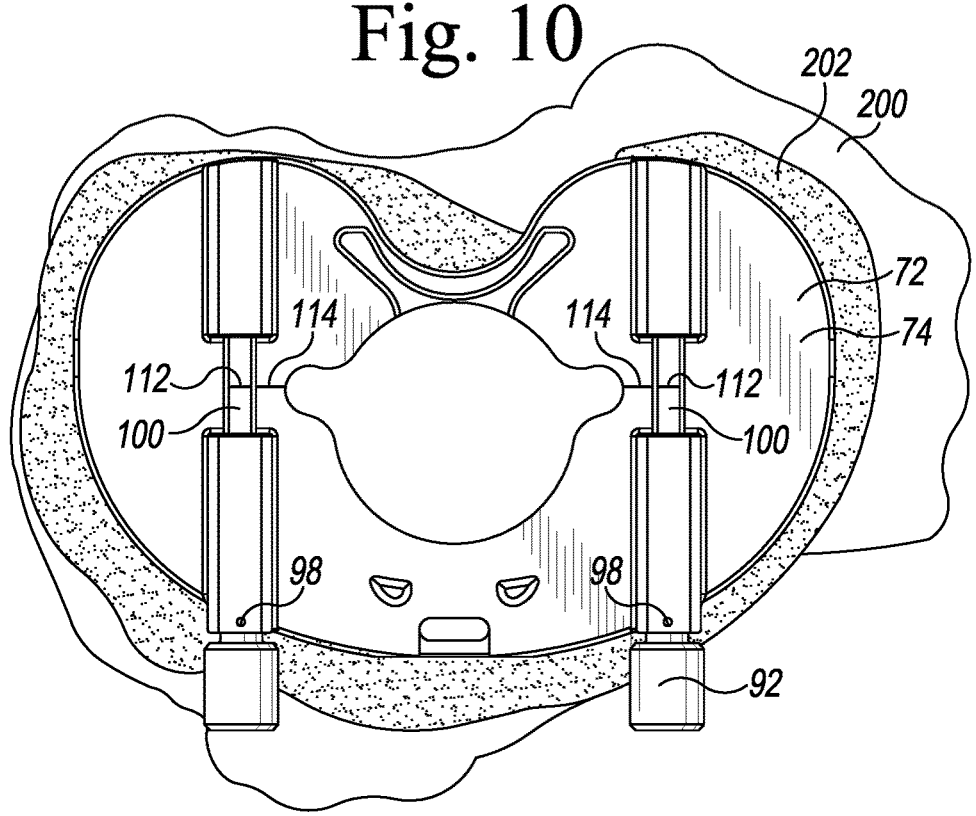
FIG. 11 is an elevation view showing the adjustable tibial trial instrument of FIGS. 2-5 installed on the resected planar surface of the patient's tibia.

As can be seen in FIGS. 2 and 11, the superior surface of both of the shuttles 100 has indicia in the form of an engraved line 112 formed therein. The upper surface 74 of the plate 72 likewise has indicia the form of an engraved line 114 formed near each of the shuttles 100. The engraved lines 112, 114 are used as a visual indicator of the neutral position of the tibial trial instrument 72. More specifically, when the engraved lines 112 of the shuttles 100 are aligned with the engraved lines 114 of the plate 74, the tibial trial instrument 72 is located in its neutral, i.e., initial, position prior to having been adjusted either rotationally or in the anterior/posterior direction. As the surgeon utilizes the thumbscrews 90 to alter the rotational and/or anterior/posterior position of the plate 74, the engraved lines 112, 114 will separate from one another as the plate 74 moves relative to the shuttles 100 with the magnitude of such separation of the lines being a visual indicator for the surgeon as to the direction and magnitude of the plate's movement.

Figure 6:
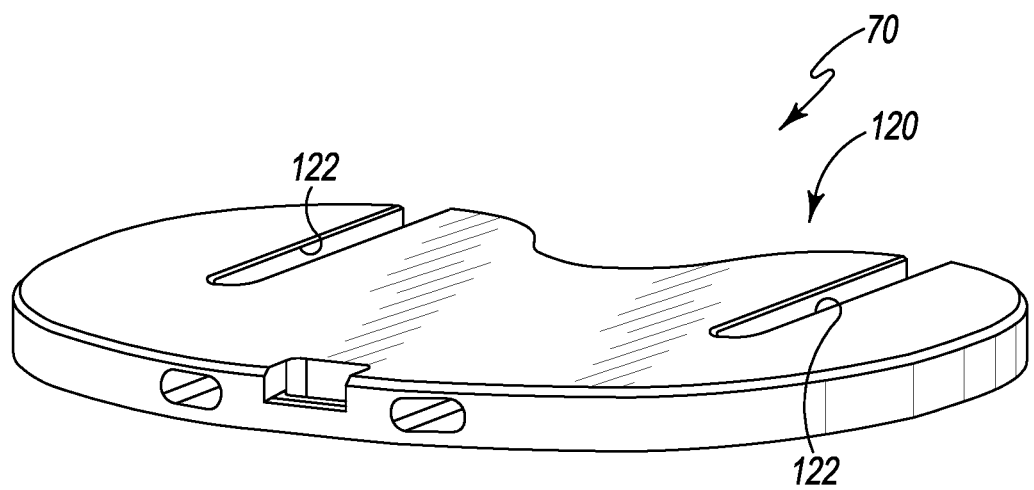
FIG. 6 is a perspective view of a sizing template.
Figure 7:
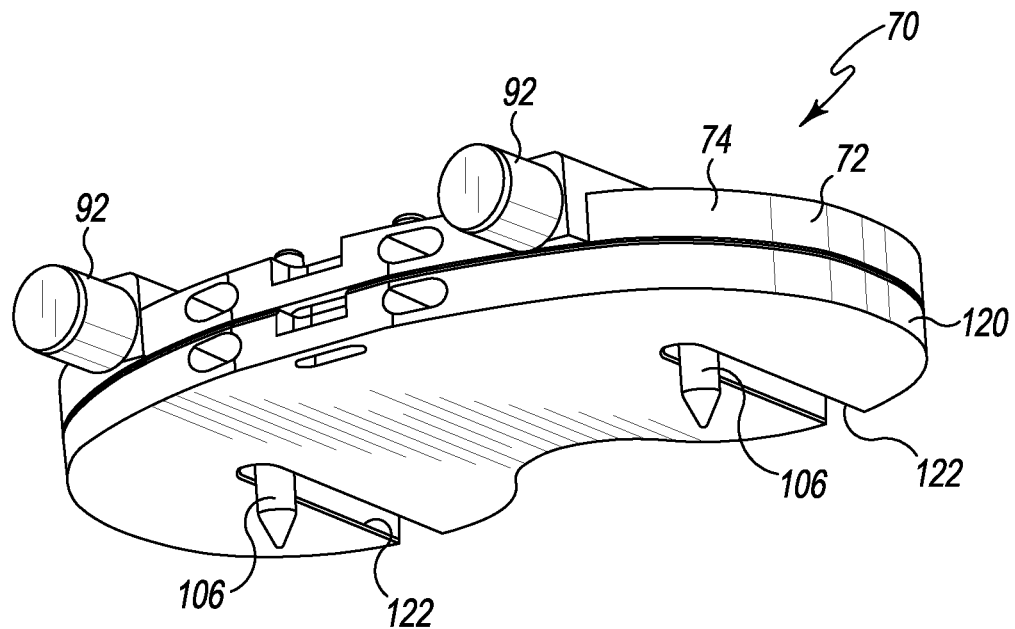
FIG. 7 is a perspective view showing the adjustable tibial trial component of FIGS. 2-5 positioned on the sizing template of FIG. 6.
Figure 8:
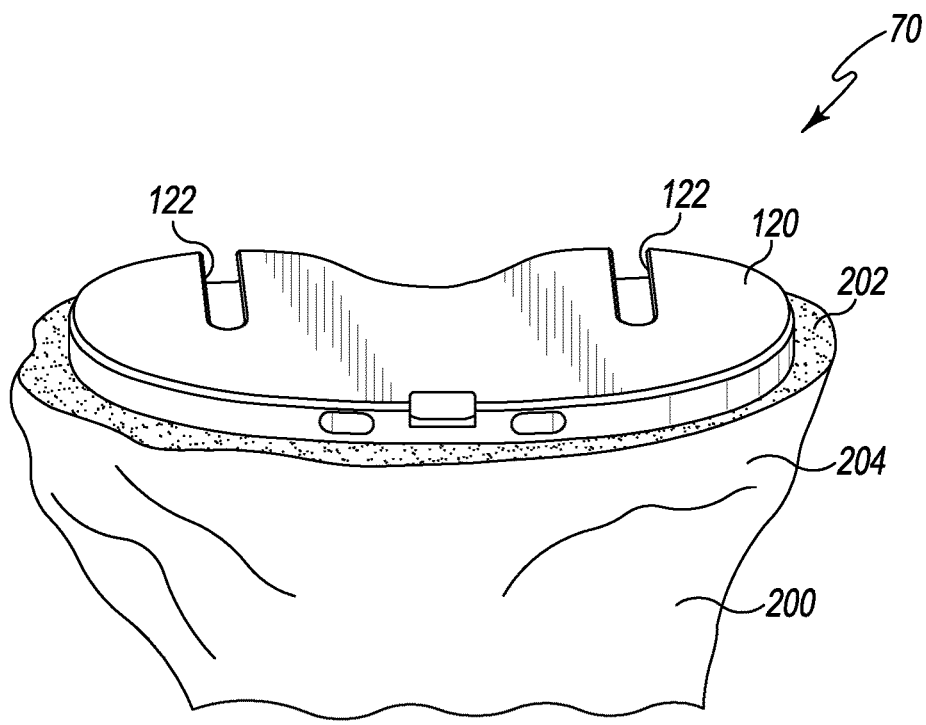
FIG. 8 is a side perspective view showing the sizing template positioned on a resected planar surface of the patient's tibia.

As shown in FIGS. 6-22, a surgeon may use the tibial trial instrument 72 during the trialing process of a surgical procedure to implant the knee prosthesis 10. To do so, as shown in FIG. 8, the surgeon initially resects the patient's tibia 200 to form a smooth planar surface 202 on a proximal end 204 of the tibia 200. The surgeon then positions a sizing template 120 on the resected planar surface 202 of the patient's tibia 200. As shown in FIGS. 6 and 7, the sizing template 120 has essentially the same size and shape as the plate 74 of the tibial trial instrument 72. A kit of sizing templates 120 of differing sizes may be used with the surgeon selecting a particular sizing template 120 that best estimates the size of the patient's tibia 200. The surgeon then places the sizing template 120 in an initial desired location and orientation on the resected planar surface 202 of the patient's tibia 200.

As can be seen in FIGS. 6 and 8, the sizing template 120 has a number of closed slots 122 formed therein. The slots 122 have a rounded anterior end, with their posterior ends opening into the posterior edge of the sizing template 120. As shown in FIG. 7, the slots 122 are sized and configured such that the spikes 106 of the tibial trial instrument 72 conform to the rounded inner end of the slots 122 when the spikes 106 are positioned in their neutral position (i.e., the engraved lines 112, 114 of the instrument align as discussed above).

Figure 9:
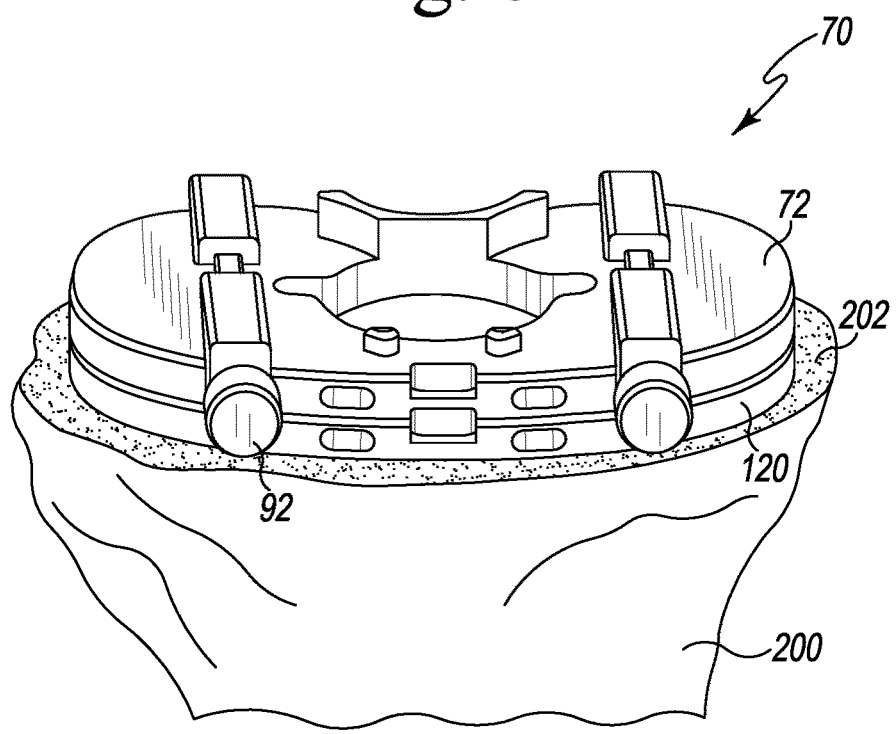
FIG. 9 is a perspective view showing the adjustable tibial trial instrument of FIGS. 2-5 being installed on the resected planar surface of the patient's tibia by use of the sizing template of FIG. 6.
Figure 10:
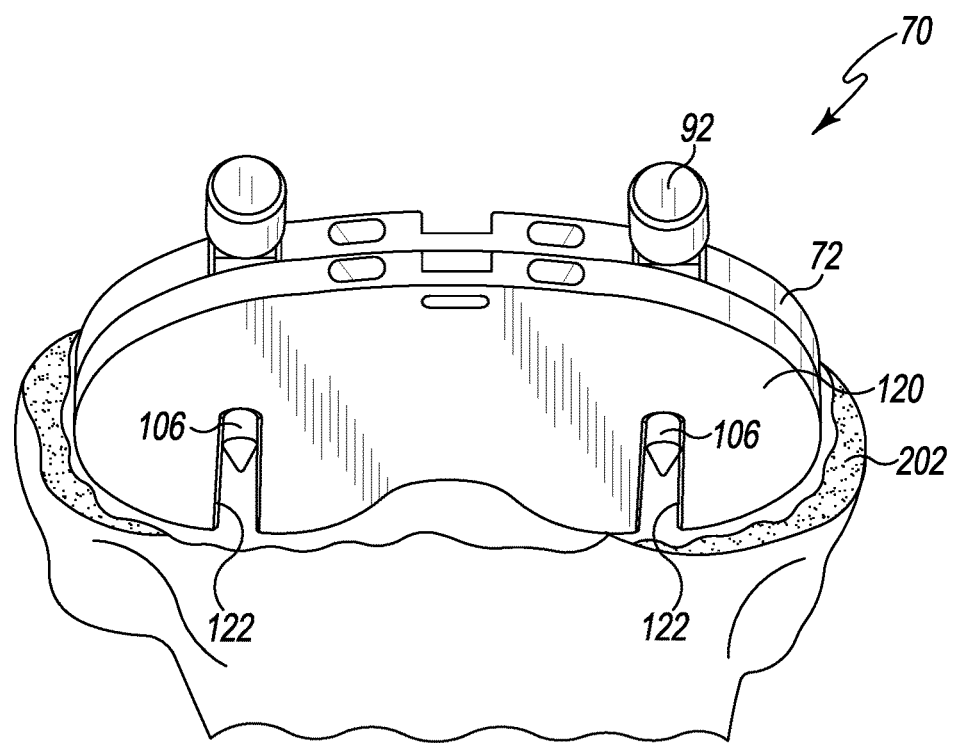
FIG. 10 is a view similar to FIG. 9 with a portion of the anterior side of the patient's tibia being illustratively removed for clarity of description.

As can be seen in FIGS. 9-11, once the sizing template 120 has been positioned in a desired position on the resected planar surface 202 of the patient's tibia 200, the tibial trial instrument 72 is then lowered, with its spikes 106 positioned in their neutral positions, onto the sizing template 120. To do so, the spikes 106 are advanced downwardly toward the resected planar surface 202 while in contact with the faces of the sizing template 120 that define the rounded anterior end of the slots 122. Doing so aligns the peripheral edges of the tibial trial instrument 72 and the sizing template 120 with one another thereby positioning the tibial trial instrument 72 in the same initial desired location and orientation on the resected planar surface 202 of the patient's tibia 200 determined by the surgeon during placement of the sizing template 120. The surgeon then impacts the tibial trial instrument 72 to advance the spikes 106 into the bone tissue of the resected planar surface 202. It should be appreciated that the sizing template 120 functions as a guide during initial impaction of the pins thereby allowing for enhanced accuracy in the installation of the tibial trial instrument 72.

Figure 12:
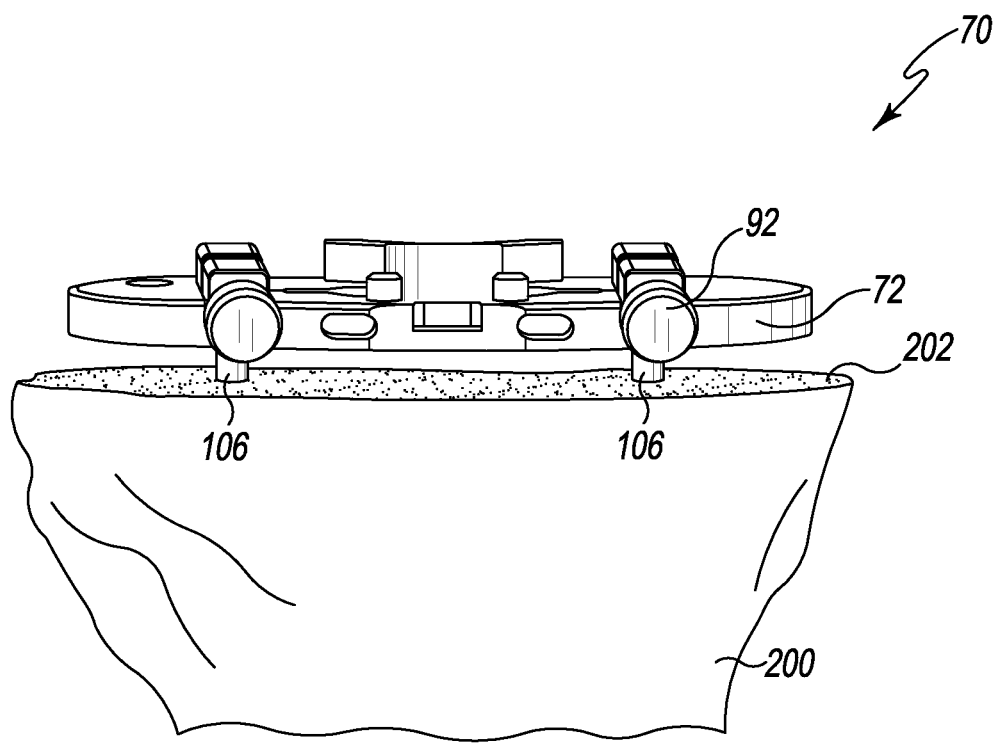
FIG. 12 is a view similar to FIG. 9, but showing the sizing template having been removed.
Figure 13:
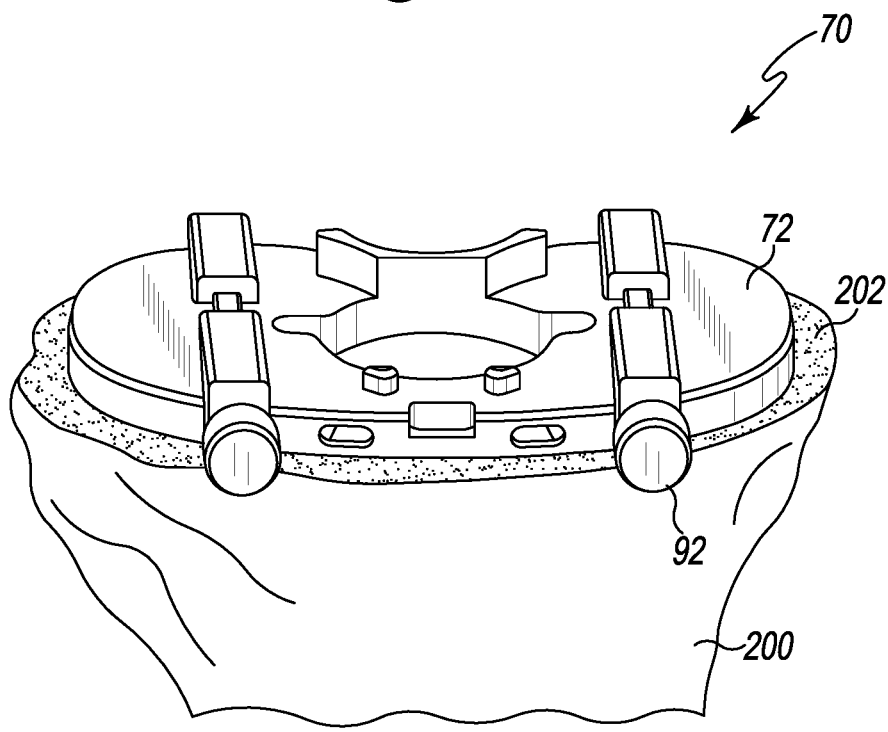
FIG. 13 is a view similar to FIG. 12, but showing the adjustable tibial trial instrument having been impacted flush on the resected planar surface of the patient's tibia.

As can be seen in FIGS. 12 and 13, once the spikes 106 have sufficiently engaged the bone tissue of the tibia 200, the sizing template 120 is removed by pulling it anteriorly such that the spikes 106 are freed through the open end of the slots 122. Once the sizing template 120 has been removed, the tibial trial instrument 72 is then further impacted until it is positioned flush on the resected planar surface 202 of the patient's tibia 200.

Figure 14:
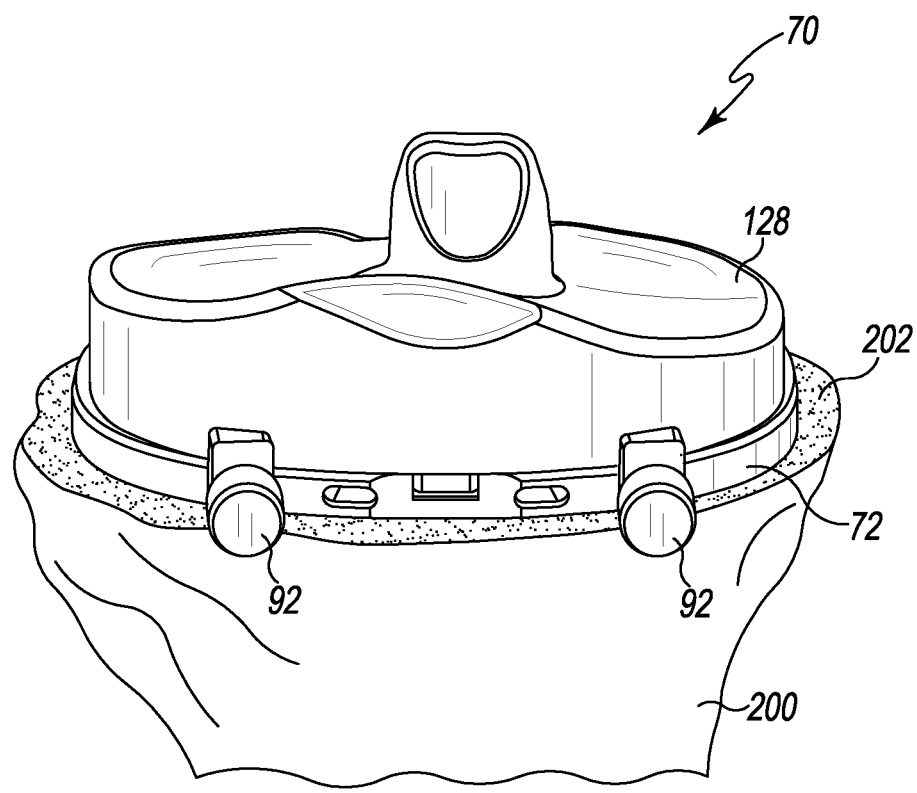
FIG. 14 is a perspective view showing the tibial trial insert installed on the adjustable tibial trial instrument.
Figure 15:
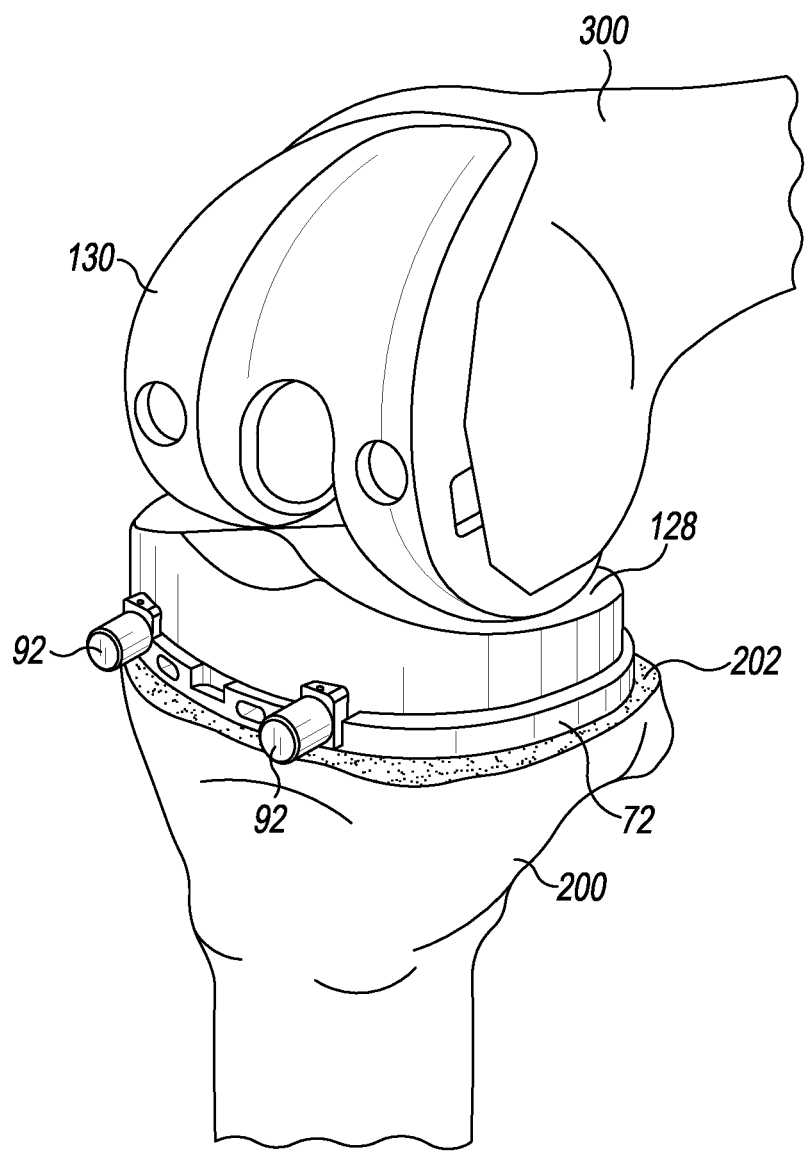
FIG. 15 is an elevational view showing a femoral trial component positioned on the distal end of the femur and the adjustable tibial trial instrument and tibial trial insert positioned on the proximal end of a tibia with the patient's knee shown positioned in full flexion.
Figure 16:
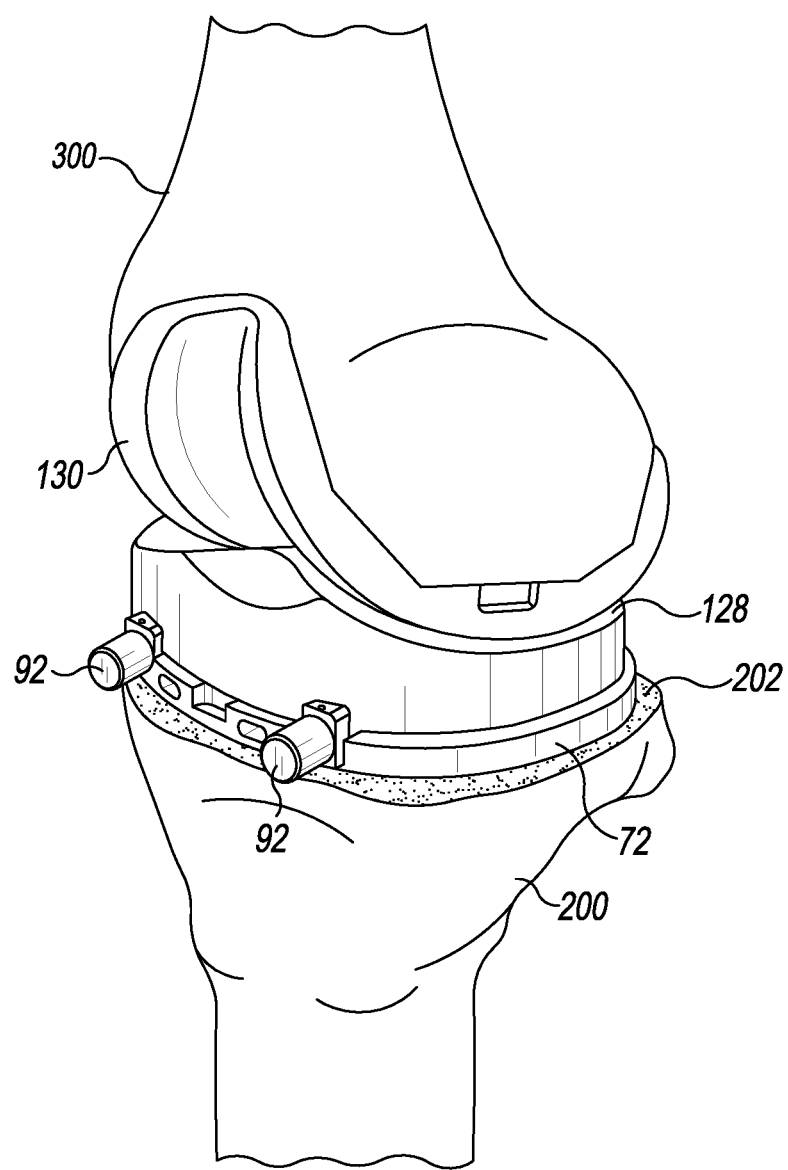
FIG. 16 is a view similar to FIG. 15, but showing the patient's knee positioned in full extension.

As shown in FIG. 14, once the tibial trial instrument 72 is fully seated on the resected planar surface 202 of the patient's tibia 200, a tibial trial insert 128 is secured thereto. With a femoral trial component 130 secured to the surgically-prepared distal end 312 of the patient's femur 310, the surgeon then moves the patient's tibia 200 relative to the patient's femur 300 between full flexion (see FIG. 15) and full extension (see FIG. 16). During such movement of the patient's knee, the surgeon evaluates the articulation of the femoral trial component 130 and the tibial trial insert 128 to determine, amongst other things, desired contact points between the two trial components 128, 130, range of motion, and cam/spine engagement. If needed, the surgeon may turn one or both of the thumbscrews 90 to adjust the rotational position of the tibial trial instrument 72 and hence the tibial trial insert 128 secured thereto. The surgeon may also use the thumbscrews 90 to adjust the anterior/posterior position of the tibial trial insert 128. Once the surgeon has adjusted the position of the tibial trial insert 128, the patient's knee may again be moved between flexion and extension and the articulation of the femoral trial component 130 and the tibial trial insert 128 revaluated. Further adjustment of the A/P position and rotational orientation of the tibial trial insert 128 by use of the thumbscrews 90 may be performed, if needed. It should be appreciated that because the thumbscrews 90 are infinitely-adjustable the surgeon is provided with a wide range of options for setting the A/P position and rotational orientation of the tibial trial insert 128 relative to the femoral trial component 130.

Figure 17:
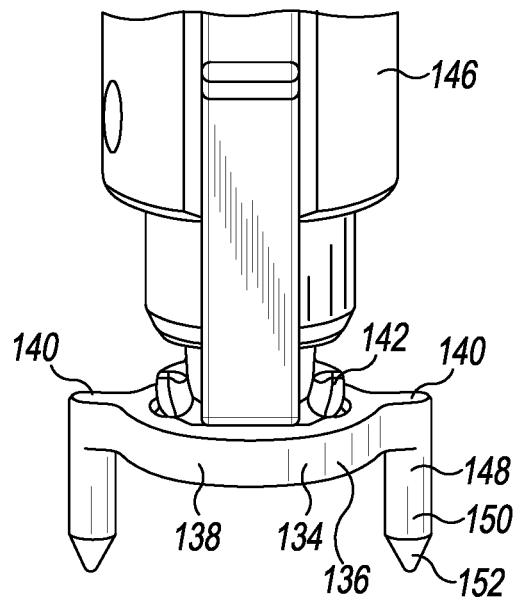
FIG. 17 is a perspective view showing the transfer button secured to the handle, note a portion of the handle has been cut away for clarity of description.
Figure 18:
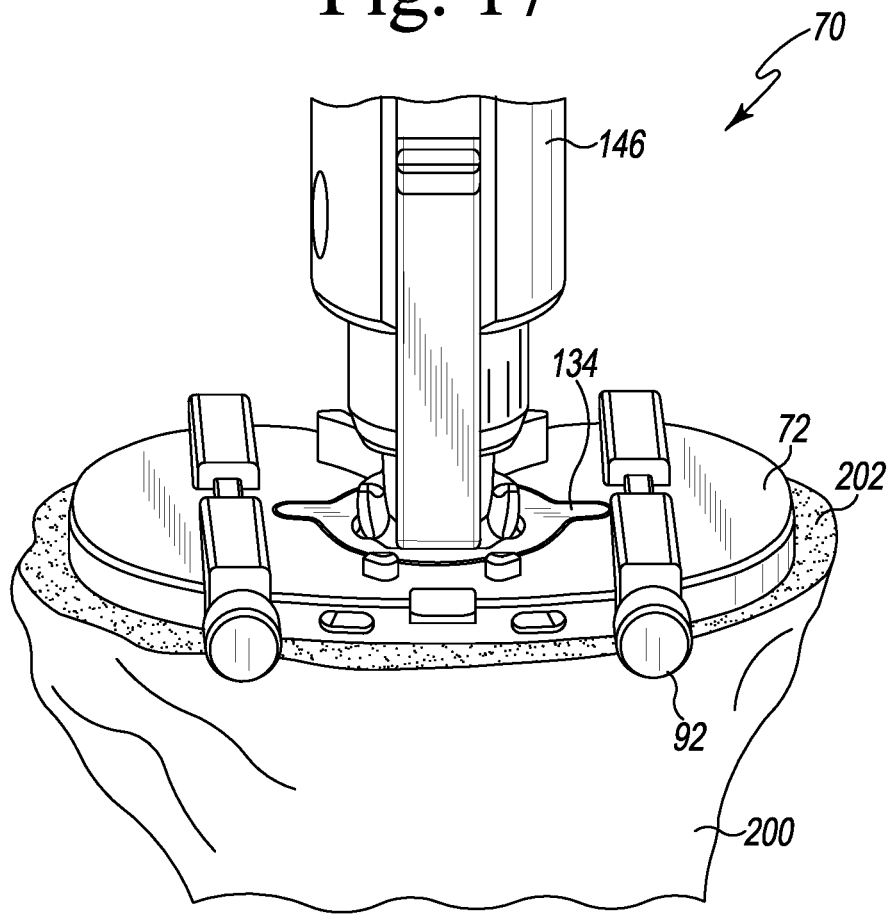
FIG. 18 is a view similar to FIG. 17, but showing the handle being used to install the transfer button.

As shown in FIGS. 17 and 18, once the trial procedure has been completed and, as a result, the tibial trial insert 128 and the tibial trial instrument 72 have been positioned in the desired A/P position and rotational orientation, the tibial trial insert 128 is removed from tibial trial instrument 72. Thereafter, a position transfer instrument or "transfer button" 134 is installed. The transfer button 134 is configured to be positioned in the plate opening 82 of the tibial trial instrument 72. The transfer button 134 has a base plate 136 that includes a central platform 138 sized to be received in the central opening 82 of the tibial trial instrument 72. The base plate 136 of the transfer button 134 also includes a pair of prongs 140 that extend outwardly from the central platform 138. The prongs 140 are sized to be received in the elongated openings 86 of the tibial trial instrument 72.

Figure 19:
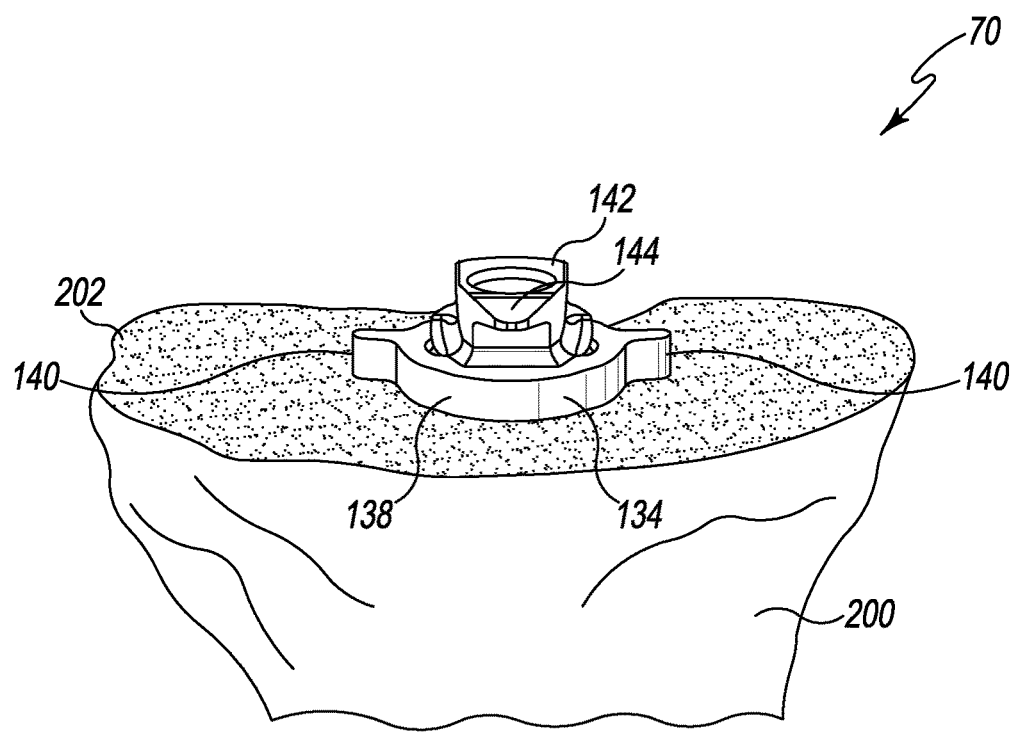
FIG. 19 is view similar to FIG. 18, but showing the adjustable tibial trial instrument having been removed from the resected planar surface of the patient's tibia.

The base plate 136 of the transfer button 134 also includes a central post 142 extending upwardly from a superior surface thereof (see also FIG. 19). The post 142 has a connector 144 formed in its superior end. The connector 144 is configured to receive a locking flange associated with an impaction handle 146 so as to secure the transfer button 134 to the handle 146 during installation and removal of the transfer button 134.

As can be seen in FIG. 17, a mounting spike 148 extends downwardly from the inferior surface of each of the transfer button's prongs 140. Each spike 148 includes an upper cylindrical section 150 and a pointed conical tip 152 configured to engage the surgically resected proximal end 202 of the patient's tibia 200 thereby temporarily securing the transfer button 134 to the proximal end 202 of the patient's tibia 200. Specifically, as shown in FIGS. 17 and 18, with the tibial trial instrument 72 positioned in the desired position and orientation determined by the surgeon, the transfer button 134 is secured to the handle 146 and positioned in alignment with the plate opening 82 of the tibial trial instrument 72. The handle 146 is then impacted by the surgeon until the inferior surface of the transfer button 134 is positioned flush on the resected planar surface 202 of the patient's tibia 200 (see FIG. 18) thereby seating the transfer button 134 within the plate opening 82.

Figure 20:
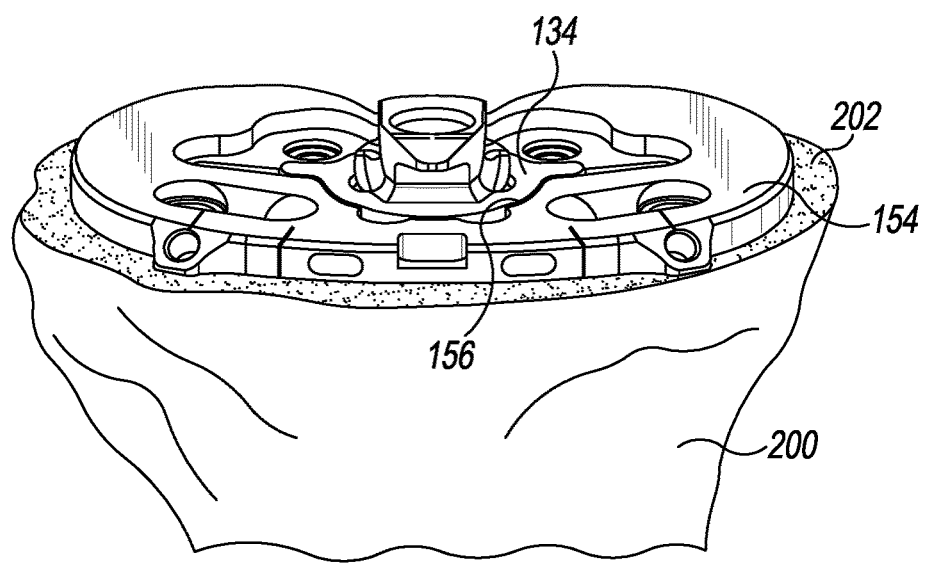
FIG. 20 is a view similar to FIG. 19, but showing the standard tibial tray trial installed over the transfer button.

As shown in FIGS. 19 and 20, once the transfer button 134 has been installed, the adjustable tibial trial instrument 72 is removed from the resected planar surface 202 of the patient's tibia 200. Thereafter, a standard tibial tray trial 154 (i.e., a non-adjustable trial) is installed over the transfer button 134. Specifically, the standard tibial tray trial 154 is lowered onto the resected planar surface 202 of the patient's tibia 200 such that the transfer button 134 is received into the plate opening 156 of the standard tibial tray trial 154. Because the plate opening 156 in the standard tibial tray trial 154 shares a similar geometry to the plate opening 82 of tibial trial instrument 72, the position and orientation of the transfer button 134 positions the standard tibial tray trial 154 in an identical position and orientation as was the previously-removed adjustable tibial trial instrument 72.

Figure 21:
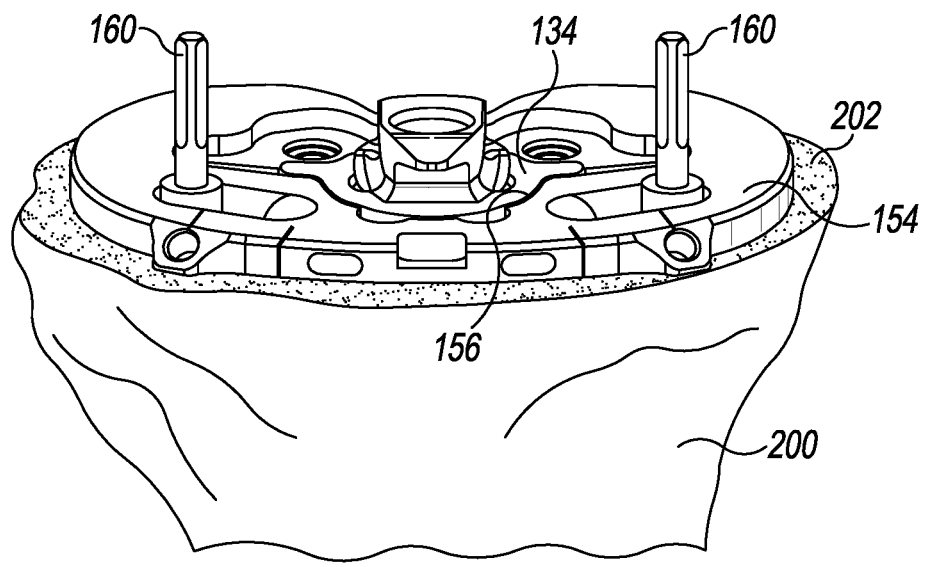
FIG. 21 is a view similar to FIG. 20, but showing the pins having been installed on the standard tibial tray trial.
Figure 22:
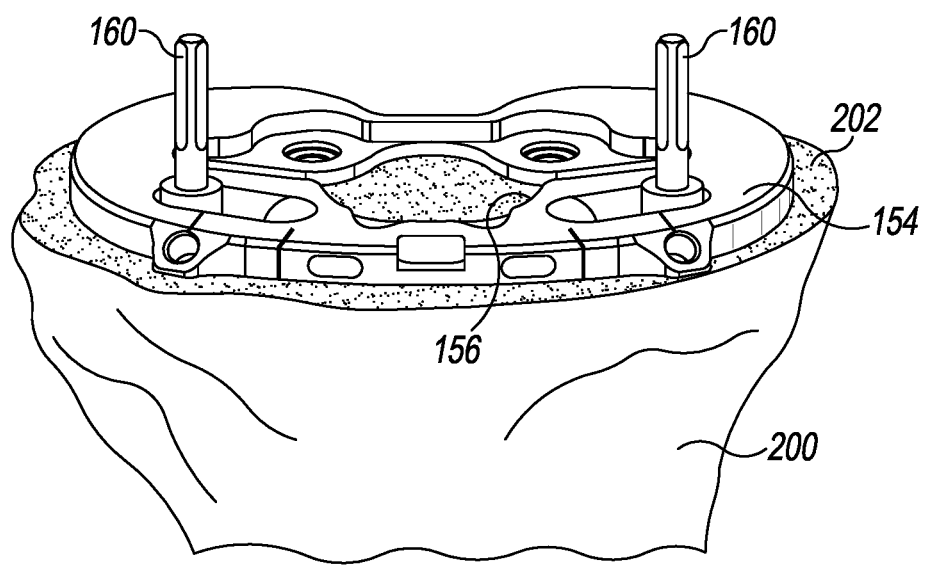
FIG. 22 is a view similar to FIG. 21, but showing the transfer button having been removed from the resected planar surface of the patient's tibia.

Once the standard tibial tray trial 154 has been installed over the transfer button 134 and is seated flush on the resected planar surface 202 of the patient's tibia 200, it is pinned to the bone by use of a pair of pins 160 (see FIG. 21). Thereafter, as shown in FIG. 22, the transfer button 134 is removed. The pinned standard tibial tray trial 154 is then used to complete the surgical preparation of the patient's tibia 200 in manner similar to as described in, for example, U.S. Pat. No. 10,195,056 which is hereby incorporated by reference. Once the patient's tibia 200 and femur 300 have both been surgically prepared, the components of the knee prosthesis 10 are then installed to complete the surgical procedure.

It should be appreciated that certain aspects of the surgical procedure described above may be altered, or even eliminated, to fit the needs of a given surgeon or instrument design. For example, in certain aspects, the tibial trial instrument 72 may be installed onto the resected planar surface 202 of the patient's tibia 200 without use of the sizing template 120. Moreover, in the case of use of certain instruments and surgical workflows, the complete tibial bone preparation procedure may be performed by use of the adjustable tibial trial instrument 72. In such an arrangement, use of the transfer button 134 and standard tibial tray trial 154 would be eliminated.

Figure 23:
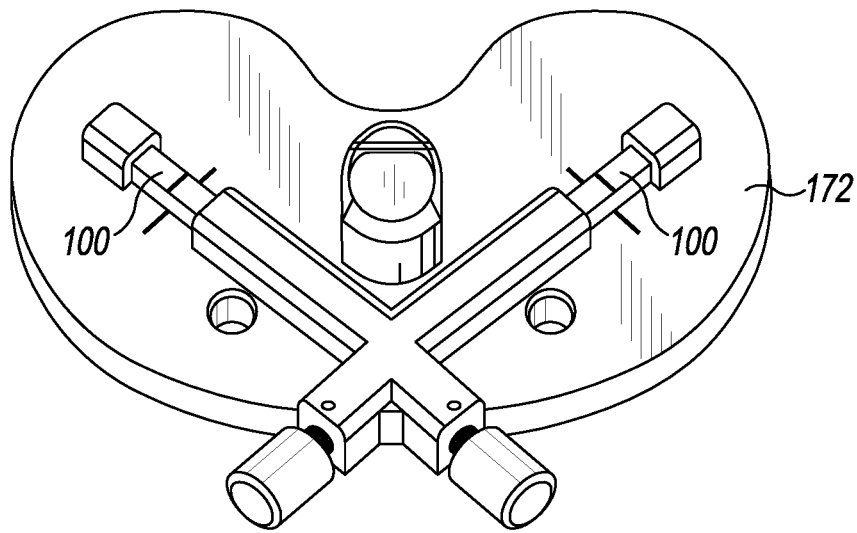
FIGS. 23 and 24 are views similar to FIG. 2, but showing additional embodiments of the adjustable tibial trial instrument.
Figure 24:
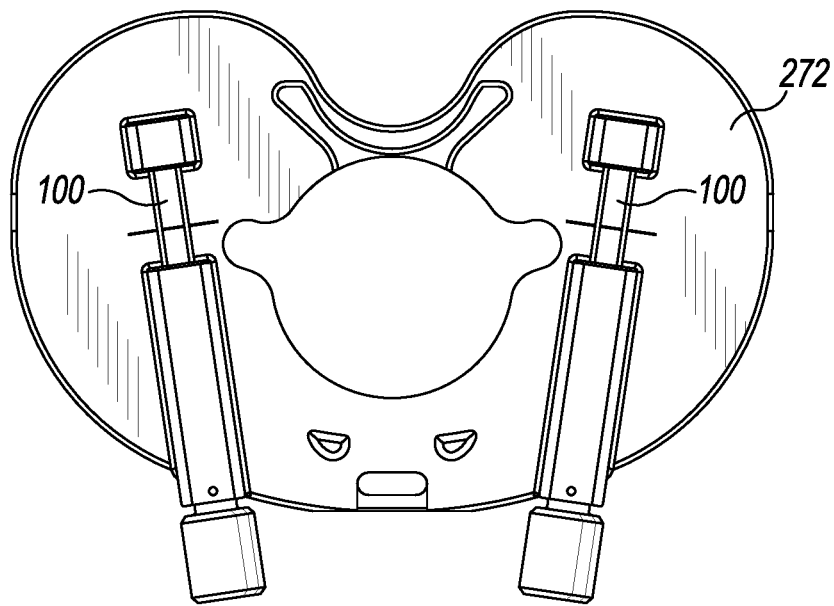

Referring to FIGS. 23 and 24, additional embodiments of the tibial trial instrument are shown. The tibial trial instruments 172, 272 of FIGS. 23 and 24 is similar to the tibial trial instrument 72 of FIGS. 2 and 3. However, the channels 88 and hence the travel of the shuttle 100 of the tibial trial instruments 172, 272 are angled relative to the anterior/posterior direction. In other words, the channels 88 have a medial/lateral slope to them as they extend from the anterior side of the instrument to its posterior side. Such an arrangement allows for infinite adjustment of the rotational and anterior/posterior position of the plate 74 of the instruments 172, 272 in a similar manner to as described above in regard to the tibial trial instrument 72. In the case of the tibial trial instrument 172 of FIG. 23, the crisscross arrangement of the channels 88 (and hence the movement of the shuttles 100) allows for a common design of the instrument 172 such that a single instrument may be used on both tibias of the patient (i.e., a common instrument can be used on both the right and left tibias of the patient).

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A method of performing an orthopaedic surgical procedure, comprising:
   positioning an attachment mechanism of an adjustable tibial trial instrument in contact with a surgically-prepared proximal end of a patient's tibia so as to secure a tibial plate of the adjustable tibial trial instrument to the surgically-prepared proximal end of a patient's tibia,
   securing a tibial insert trial to the adjustable tibial trial instrument,
   securing a femoral trial component to a surgically-prepared distal end of the patient's femur,
   positioning the femoral trial component into contact with the tibial insert trial,
   moving the patient's tibia relative to the patient's femur through a trial range of motion, and
   operating an adjustment mechanism of the adjustable tibial trial instrument, with the tibial insert trial secured to the adjustable tibial trial instrument, so as to (i) move the tibial insert trial relative to the surgically-prepared proximal end of the patient's tibia in the anterior/posterior direction, and (ii) rotate the tibial insert trial relative to the surgically-prepared proximal end of the patient's tibia.

2. The method of claim 1, wherein operating the adjustment mechanism of the adjustable tibial trial instrument comprises rotating one or both of a pair of knobs of the adjustable tibial trial instrument so as to move the tibial insert trial relative to the surgically-prepared proximal end of the patient's tibia.

3. The method of claim 1 wherein securing the adjustable tibial trial instrument to the surgically-prepared proximal end of the patient's tibia comprises:
   positioning a sizing template on the surgically-prepared proximal end of the patient's tibia,
   advancing a pair of bone-engaging spikes of the adjustable tibial trial instrument into a pair of slots formed in the sizing template,
   impacting the adjustable tibial trial instrument so as to drive the bone-engaging spikes into the surgically-prepared proximal end of the patient's tibia to an initial depth,
   removing the sizing template from the surgically-prepared proximal end of the patient's tibia, and
   impacting the adjustable tibial trial instrument so as to drive the bone-engaging spikes into the surgically-prepared proximal end of the patient's tibia to a final depth.

4. The method of claim 1, further comprising:
   positioning a position transfer instrument in a plate opening defined in the adjustable tibial trial instrument and thereafter impacting the position transfer instrument so as to secure it to the surgically-prepared proximal end of the patient's tibia,
   removing the adjustable tibial trial instrument from the surgically-prepared proximal end of the patient's tibia, and
   positioning a non-adjustable tibial trial instrument on the surgically-prepared proximal end of the patient's tibia such that the position transfer instrument is received into a plate opening defined in the non-adjustable tibial trial instrument and thereafter securing the non-adjustable tibial trial instrument to the surgically-prepared proximal end of the patient's tibia.

* * * * *